United States Patent
McGhee et al.

(10) Patent No.: US 6,767,551 B2
(45) Date of Patent: Jul. 27, 2004

(54) COATING FOR USE WITH MEDICAL DEVICES AND METHOD OF MAKING SAME

(75) Inventors: Diane McGhee, Hazelwood, MO (US); Scott M. Britton, Ballwin, MO (US); Elizabeth Lagwinska, Chesterfield, MO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/929,908

(22) Filed: Aug. 15, 2001

(65) Prior Publication Data

US 2003/0044451 A1 Mar. 6, 2003

(51) Int. Cl.$^7$ ................................................. A61K 9/00
(52) U.S. Cl. ....................... 424/426; 424/423; 424/422; 424/425
(58) Field of Search ............................... 424/400, 422, 424/423, 426, 425, 484

(56) References Cited

U.S. PATENT DOCUMENTS

| | | | |
|---|---|---|---|
| 3,939,049 A | 2/1976 | Ratner et al. | 204/159.13 |
| 3,975,350 A | 8/1976 | Hudgin et al. | 260/30.4 |
| 3,987,497 A | 10/1976 | Stoy et al. | 3/1 |
| 4,054,139 A | 10/1977 | Crossley | 128/260 |
| 4,100,309 A | 7/1978 | Micklus et al. | 427/2 |
| 4,119,094 A | 10/1978 | Micklus et al. | 128/132 |
| 4,592,920 A | 6/1986 | Murtfeldt | 427/2 |
| 4,603,152 A | 7/1986 | Laurin et al. | 604/265 |

FOREIGN PATENT DOCUMENTS

EP 0328421 * 8/1989

OTHER PUBLICATIONS

Remington's Pharmaceutical Sciences, Eighteenth Edition, 1990, pp. 1286–1329.*

* cited by examiner

Primary Examiner—Thurman K. Page
Assistant Examiner—Rachel M. Bennett
(74) Attorney, Agent, or Firm—Mark S. Leonardo; John C. Serio; Brown Rudnick Berlack Israels LLP

(57) ABSTRACT

The inventive coating may be employed to deliver a pharmaceutical agent to a selected body area that is involved within the insertion or application of a medical device. Such medical devices may include silicone based urinary catheters and other medical implants as well as other silicone based devices having deformable portions which could benefit from the release of a pharmaceutical agent from its surface. The coating allows the introduction of the pharmacological additive having a release rate that is within acceptable pharmacokinetic criteria. The release rate is adjusted by utilizing different salt forms of the additive and adjusting the concentration of urethane and RTV silicone. The coating incorporates additive compounds such as anti-microbial, anti-fungals and other organic compounds. Methods are also provided for the manufacture of the subject coating and for the application of the same to surfaces of medical devices.

41 Claims, No Drawings

COATING FOR USE WITH MEDICAL DEVICES AND METHOD OF MAKING SAME

BACKGROUND

1. Technical Field

The present disclosure relates to a coating for silicone based medical devices, and more particularly, to a coating which allows a pharmaceutical agent to be released from an internal and/or external surface of such medical devices.

2. Background of the Related Art

Various medical devices that are inserted into body cavities of humans and animals can unfortunately introduce bacterial, viral and fungal infections into these body cavities. Numerous coatings are available for medical devices that employ polyurethane or urethane pre-polymers to act as lubricants, drug delivery systems and the like. Known coatings applied to surfaces of medical devices include coatings of polyvinylpyrrolidone, polyurethane, acrylic polyester, vinyl resin, fluorocarbons, silicone rubber, and combinations of these substances. For example, U.S. Pat. Nos. 4,100,309 and 4,119,094 to Micklus et al., relate to a hydrophilic coating of polyvinylpyrrolidone-polyurethane interpolymer formed using polyisocyanate. To prevent infections, various anti-microbial methods and compositions have been disclosed in U.S. Pat. Nos. 4,054,139; 4,592,920 and 4,603,152. Additionally, U.S. Pat. No. 3,939,049 to Ratner et al. relate to a method of grafting hydrogels for lubrication to polymeric substrates using radiation, U.S. Pat. No. 3,975,350 to Hudgin et al. relate to hydrophilic polyurethane polymers for use as lubricants and U.S. Pat. No. 3,987,497 to Stoy et al. relate to a tendon prosthesis having a lubricant hydrogel coating.

While the above coatings are appropriate for application to urethane, polyvinylchloride (PVC), steel or polyesters, these systems offer poor adherence to silicone medical devices unless the silicone surface is subjected to corona or plasma treatment. The need to pre-treat these silicone based medical devices limits coatings to surfaces that are pre-treated by the above methods, resulting in additional manufacturing process steps, additional costs and variability of the medical device. Additionally, the above methods have not been adequate as performance of the coatings has been unsatisfactory over flexible or expandable segments of medical devices such as catheter balloons.

Known silicone medical devices have been coated by a co-extrusion of silicone rubber and by room temperature vulcanizing ("RTV") silicone. Silane coupling agents have also been employed to attach coatings and compounds to silicone rubber medical devices. However, these methods do not overcome the inherently poor drug delivery properties of silicone. These problematic silicone drug delivery properties include poor diffusion of the drug in a hydrophobic environment and surfaces that resist subsequent application of a hydrophilic bolus coating or lubricious coating.

To solve these and other potential disadvantages of known methods for coating silicone medical devices, a coating is needed that will allow effective drug delivery from surface areas of silicone medical devices. Desirably, the coating is flexible to retain adhesion over an expandable portion of a silicone medical device. Coatings are needed for silicone medical devices having a broad range of applications, including accommodating the proper delivery of medicinal agents ranging from inorganic silver salts to antibiotics. Furthermore, it is desirable to produce a coating that will eliminate additional manufacturing steps that require surface pre-treatment resulting in excessive cost.

SUMMARY

The inventive coating may be employed to deliver a pharmaceutical agent to a targeted tissue, releasing a pharmaceutical agent from the surface of a coated medical device, the surface of which is in contact with the target tissue. Therefore, the inventive coating may incorporate additives such as anti-microbial, anti-fungal and phytochemical having medicinal or like properties. Methods are provided for manufacture of the inventive coating and its application to medical device surfaces.

As is described in greater detail below, the present disclosure provides a coating composition including a combination of RTV silicone and urethane. The combination of RTV silicone and urethane produces an inventive coating that facilitates drug delivery and enhances adherence to a flexible silicone medical device. The inventive coating provides adherence over highly expanded surfaces such as, for example, catheter balloons, etc.

The present disclosure provides a method of making the subject coating that adheres to a wide variety of flexible silicone devices. The coating is chemically stable, biocompatible and eliminates additional manufacturing requirements for surface pre-treatment. The coating allows effective drug delivery from a flexible silicone medical device that accommodates a broad spectrum of medicinal agents ranging from inorganic silver salts to antibiotics.

DETAILED DESCRIPTION OF EXEMPLARY EMBODIMENTS

The disclosed exemplary embodiments and examples of use and operation are discussed in terms of medical device coatings, and more particularly, in terms of coatings for the internal and/or external surfaces of silicone-based medical devices which facilitate release of pharmaceutical agents from such coated surfaces to targeted tissues. The inventive medical device coatings are useful in a wide variety of coatings and devices employable in the medical field including, those used during invasive procedures, as well as, topical, dental and veterinary coatings and devices.

The following discussion describes inventive coatings for deformable surfaces of silicone-based medical devices and coatings that facilitate release of medicinal agents from such coated surfaces. Reference will now be made in detail to the non-limiting exemplary embodiments of the disclosure, which are illustrated herein and in the accompanying examples.

The inventive coatings include a combination of RTV, silicone and urethane. The combination advantageously provides a coating that is flexible and retains adhesion with a deformable surface of the silicone-based medical device. The coating adheres to the deformable surface during flexure or expansion of the device, such as, for example, catheter balloons, etc. Solvent selection in preparing the inventive coatings is based on providing adequate solubility and compatibility to the urethane, silicone and additives. The urethanes in the coatings are selected from the group of aromatic urethanes, including, but not limited to those derived from 4,4-methylenediphenol diisocyanante, 1,4-butanediol and polytetramethylene glycol (i.e., Pecoflex®). Additional polyurethanes include: Pellethane®, an aromatic ether polyurethane manufactured by Dow Chemical; Hyrothane®, manufactured by CardioTech International; and Tecoflex®, an aliphatic urethane manufactured by Thermedics, Inc. Other known urethanes are contemplated.

Polyurethane in the coating increases the binding strength and controls the rate of release of any active ingredient, permitting release rates for anti-microbial or other medicinal additives to be engineered to perform within desired parameters and rates. The polyurethane imparts adherence properties to the coating allowing its adhesion to deformable surfaces of silicone based medical devices. Since different urethanes have different properties and may require different solvent systems, appropriate solvent selection and blend ratio is desirable to ensure adequate solubility and compatibility to urethane and additives.

Without limitation, preferred RTV silicones are moisture-cure elastomers desirably derived from acyloxy-, alkoxy-, and methoxy-curing systems. The examples include but are not limited to methyltri-methoxy silane (GE RTV 142) or methyltri-acetoxy silane (GE RTV-108). Additional RTV silicones include, but are not limited to, Dow Corning 3140 RTV, Wacker RTV SWS951 and Nusil Med10-6605. Other alternative silanes include tetrachlorosilane, vinyl trimethoryl silane, organosilane ester tris[3-(trimethoxysilyl)propyl] isocyanurate, bis[trimethoxysilyl)propyl] amine and gamma-ureidopropyltrimethoxy silane. While these silanes impart more desirable coating properties compared with coatings using urethane alone, they do not possess the adherent properties of RTV silicones.

RTV silicones dissolve in solvents such as, for example, toluene, hexane, xylene, tetrahydrofuran (THF), cyclohexanone. Medicinal additives dissolve in solvents such as n-Methypyrrolidinone (NMP), and alkylesters of a carboxylic acid C1–12 alkylesters, such as ethyl lactate. In an illustrative embodiment, the coating ingredients dissolve in n-NMP, THF or THF/cyclohexanone mixture as these solvents are appropriate for all coating components. Other known solvents that are compatible to the coating components are contemplated.

Anti-microbial additives in the inventive coatings include the biguanides, especially chlorhexidine and its salts, including chlorhexidene acetate, chlorhexideine gluconate, chlorhexidine hydrochloride, and chlorhexidine sulfate, silver and its salts, including silver acetate, silver benzoate, silver carbonate, silver iodate, silver iodide, silver lactate, silver chloride, silver laurate, silver nitrate, silver oxide, silver palmitate, silver protein, and silver sulfadiazine, polymyxin, tetracycline, aminoglycosides, such as tobramycin and gentamicin, rifampician, bacitracin, neomycin, chloramphenical, quinolone such as oxolinic acid, norfloxacin, nalidix acid, pefloxacin, enoxacin and ciprofloxacin, penicillins such as ampicillin, amoxicillin and piracil, cephalosporins, vancomycin, and combinations of any of the above anti-microbials. These anti-microbial agents can be incorporated singularly, or in combination with other additives.

Optionally, 0–5% but preferably 1–3% of an anti-fungal agent can be added to the coating. Suitable anti-fungal agents include, but are not limited to: tolnaftate, miconazole, fluconazole, clotrimazole, econazole, ketoconazole, itraconazole, terbinafine, and polyene anti-fungal agents such as amphotericin, nystatin and natamycin. These anti-fungal agents can be incorporated singularly or in combination with other additives.

Optionally, 0–5% but preferably 1–3% of organic compounds derived from plants and herbs having desirable pharmacological properties are utilized. Extracts of plants and herbs are known to possess anti-microbial activity and their use is safe for human and animal consumption. Extracts of such plants, known as phytochemicals, may be utilized for their anti-microbial properties. Some of these extracts, such as grapefruit seed extract, tea tree oil and myrtle oil and others can be incorporated into the inventive coating vehicle and their anti-microbial properties released to the surrounding tissue in an efficacious manner. These organic compounds can be incorporated singularly or in combination with other additives.

These illustrative embodiments contemplate known colorants, emulsifiers, surfactants, and color stabilizers that can be added to the inventive coating. The colorants in the form of dyes or pigments aid in reducing shelf life or sterilizing discoloration. Color stabilizers may be used when the anti-microbial is a silver salt. The addition of emulsifiers and surfactants aid in suspension stability of the additive within the coating and include ethoxylated fatty acids and glycol mono and diesters of fatty acids. The emulsifiers include but are not limited to ethylene glycol disterate and ethylene glycol monosterate or other surfactants that belong to the same chemical families. These emulsifiers are used to change the hydrophilicity of the coating and facilitate pharmaceutical delivery rate adjustment. An active ingredient, for example, anti-microbials including silver salts or antibiotics, may be uniformly suspended in the coating solution by the addition of an emulsifier. Contact with moisture releases these active ingredients. The modification of urethane to silicone ratio (weight to weight) and addition of emulsifiers further adjust medicinal agent release rates.

The inventive coatings are generally prepared by first obtaining several mixing vats in which intermediate solutions are prepared that, when further reacted, form the coating composition. The mixing vats should be dry and free of water and solvents. The coating composition is preferably blended at room temperature according to the following component ratios (in weight percent): 0.5 to 10 (preferably 1.5) weight percent RTV silicone, 1 to 10 (preferably 3.0) weight percent polyurethane, 0.1 to 3.0 (preferably 0.25) weight percent emulsifier and 77 to 99 (preferably 92.25) weight percent solvent. The coating ingredients are dissolved in a solvent such as THF or THF/cyclohexanone or other known solvents.

The resulting coating solution appears cloudy. The coating solution increases in viscosity due to solvent evaporation if not tightly capped during storage. For best results, prior to coating medical devices with the inventive coating solution, a particular medical device, for instance a catheter, should be cleaned by first filling a container with a solvent utilized in the formulation of the coating. The medical device is dip washed in the solvent for approximately 5 seconds and dried by forced air at approximately 50 to 90° C. to remove surface residual solvent and debris. The medical device, at this point, is completely solvent free. The medical device is dip coated for about 5 to 30 seconds in the coating vehicle solution and slowly removed from the solution vat at a rate of about 0.5 inches per second. The medical device is preferably baked in forced air ovens at approximately 50° to 90°+/−5° C. for approximately 30 minutes to 3 hours but most preferably for 60 minutes and removed from the oven and air dried at room temperature for 24 hours. Curing temperature and time are dependent upon the RTV silicone and varies according to concentrations. The medical devices are preferably checked for uniformity and to ensure that no solvent odor is present.

Illustrative embodiments regarding the methods of making and using the coating vehicle of the present disclosure are described in greater detail in the following examples, provided for purposes of further illustration. The following examples are not intended to be construed as limiting the scope of the present disclosure.

EXAMPLE 1

A drug delivery coating for silicone medical devices is prepared by blending at room temperature the following components in three separate containers. In a first container, THF, Pellethane® and an emulsifier are mixed for at least 2–3 hours until the Pellethane® is fully dissolved forming a first solution. In a second container, NMP and norfloxacin are mixed for approximately 20 minutes forming a second solution. In a third container, tolnaftate is mixed for approximately 10 minutes with THF until the tolnaftate is dissolved forming a third solution. The second solution is added to the first solution and mixed for approximately 5–10 minutes. The third solution is added to the combination of the first and second solutions and the combined solutions are mixed for approximately 15 minutes. Prior to coating the medical device, the RTV/Silane is added to the combined solutions and mixed for approximately one hour.

| | | |
|---|---|---|
| THF | 29.75 g | First Container |
| Urethane | 3 g | |
| Emulsifier | 0.25 g | |
| NMP | 30 g | Second Container |
| Norfloxacin | 1 g | |
| THF | 33.2 g | Third Container |
| Tolnaftate | 1 g | |
| RTV/Silane | 1.8 g | |

EXAMPLE 2

A drug delivery coating for silicone medical devices is prepared by blending at room temperature the following components in three separate containers. In a first container, THF, Pellethane® and an emulsifier are mixed for at least 2–3 hours until the Pellethane® is fully dissolved forming a first solution. In a second container, NMP and norfloxacin are mixed for approximately 20 minutes forming a second solution. In a third container, clotrimazole is mixed for approximately 10 minutes with THF until the clotrimazole is dissolved forming a third solution. The second solution is added to the first solution and mixed for approximately 5–10 minutes. The third solution is added to the combination of the first and second solutions and the combined solutions are mixed for approximately 15 minutes. Prior to coating the medical device, the RTV/Silane is added to the combined solutions and mixed for approximately one hour.

| | | |
|---|---|---|
| THF | 29.75 g | First Container |
| Urethane | 3 g | |
| Emulsifier | 0.25 g | |
| NMP | 30 g | Second Container |
| Norfloxacin | 1 g | |
| THF | 33.2 g | Third Container |
| Clotrimazole | 1 g | |
| RTV/Silane | 1.8 g | |

EXAMPLE 3

A drug delivery coating for silicone medical devices is prepared by blending at room temperature the following components in three separate containers. In a first container, THF, Pellethane® and an emulsifier are mixed for at least 2–3 hours until the Pellethane® is fully dissolved forming a first solution. In a second container, NMP and norfloxacin are mixed for approximately 20 minutes forming a second solution. In a third container, RTV/Silane is mixed for approximately one hour with THF until the RTV/Silane is dissolved forming a third solution. The second solution is added to the first solution and mixed for approximately 5–10 minutes. The third solution is added to the combination of the first and second solutions and the combined solutions are mixed for approximately one hour.

| | | |
|---|---|---|
| THF | 29.75 g | First Container |
| Urethane | 3 g | |
| Emulsifier | 0.25 g | |
| NMP | 25 g | Second Container |
| Norfloxacin | 1 g | |
| THF | 40 g | Third Container |
| RTV/Silane | 1 g | |

EXAMPLE 4

A drug delivery coating for silicone medical devices is prepared by blending at room temperature the following components in two separate containers. In a first container, THF, Pellethane® and an emulsifier are mixed for at least 2–3 hours until the Pellethane® is fully dissolved forming a first solution. In a second container, RTV/Silane and THF are mixed for approximately one hour forming a second solution. The second solution is added to the first solution and mixed for approximately 5–10 minutes. The container, containing the combined solutions, is wrapped with an opaque material and a silver salt is added and mixed for approximately one hour until fully dissolved.

| | | |
|---|---|---|
| THF | 29.75 g | First Container |
| Urethane | 3 g | |
| Emulsifier | 0.25 g | |
| RTV/Silane | 1 g | Second Container |
| THF | 64 g | |
| Silver salt | 2 g | |

EXAMPLE 5

A drug delivery coating for silicone medical devices is prepared by blending at room temperature the following components in two separate containers. In a first container, THF, Pellethane® and an emulsifier are mixed for at least 2–3 hours until the Pellethane® is fully dissolved forming a first solution. In a second container, RTV/Silane and THF are mixed for approximately one hour forming a second solution. The second solution is added to the first solution and mixed for approximately 5–10 minutes. A phyto-chemical compound is added to the combined solutions and mixed for approximately one hour.

| | | |
|---|---|---|
| THF | 29.75 g | First Container |
| Urethane | 3 g | |
| Emulsifier | 0.25 g | |
| RTV/Silane | 1 g | Second Container |
| THF | 63 g | |
| Phyto-chemical compound | 3 g | |

The anti-bacterial efficacy of the coatings in examples 1, 2, 3 and 5 are summarized in table one below. The coatings having a medicinal compound produced within these examples exhibit significant zones of inhibition within the various cultures. The efficacious nature of the coating is further demonstrated in that the control test segment having no medicinal compound exhibits no zone of inhibition. The test data is reflective of measurements recorded 24 hours after the test segment is placed in contact with the culture of interest.

TABLE 1

| Organism | Coated Test Segment w/Medicinal Compound | Coated Test Segment w/out Medicinal Compound |
| --- | --- | --- |
|  | Zone of Inhibition* | Zone of Inhibition* |
| E. coli | 5 mm–15 mm | 0 |
| S. aureus | 7 mm–15 mm | 0 |
| P. aeruginosa | 3 mm–10 mm | 0 |
| C. albicans | 3 mm–18 mm | 0 |

*Zones are recorded in mm, radius.

The anti-bacterial efficacy of the coating in example 4 is summarized in table two below. While the test segment without a medicinal compound exhibits no reduction in anti-bacterial growth, the coating with a medicinal compound exhibits significant anti-bacterial action against the various cultures of interest. The test data summarized in table 2 is reflective of measurements recorded 24 hours after the test segment is placed in contact with the culture of interest.

TABLE 2

| Organism | Coated Test Segment w/Medicinal Compound | Coated Test Segment w/out Medicinal Compound |
| --- | --- | --- |
| E. coli | 1–3 log reduction* | 1–2 log increase |
| S. aureus | 1–3 log reduction | 1–2 log increase |
| P. aeruginosa | 1–2 log reduction | 1–2 log increase |
| C. albicans | 1–2 log reduction | 1–2 log increase |

*Denotes a decrease in culture growth.

Although the coatings described in the illustrative embodiments herein are a series of coatings having adhesion to deformable portions of silicone based medical device and pertaining to anti-microbial and anti-fungal additives and the methods for ensuring that the pharmacokinetics are within efficacious ranges, it should be appreciated that additives within the coating vehicle could be other desirable pharmaceutical active compounds such as topical anesthetics, anti-inflammatory compounds both non-steroidal and steroidal, spermicidal compounds, or the like. Similarly, rather than the traditional pharmaceutical compounds, the additives can include organic compounds with desired pharmacological effects.

The foregoing describes specific embodiments of the inventive coatings and process for preparing. The present disclosure is not limited in scope by the illustrative embodiments described, which are intended as specific illustrations of individual aspects of the disclosure. Functionally equivalent methods and components are within the scope of the disclosure. Indeed, the instant disclosure permits various and further modifications to the preferred embodiments, which will become apparent to those skilled in the art. Such modifications are intended to fall within the scope of the appended claims.

What is claimed is:

1. A flexible coating for a medical device, the coating comprising: RTV silicone and urethane, wherein said RTV silicone is selected from the group consisting of methyltri-methoxy silane, methyltri-acetoxy silane, tetrachlorosilane, vinyl trimethoryl silane, organosilane ester tris[3-trimethoxysilyl)propyl] isocyanurate, bis[trimethoxysilyl)propyl] amine and gamma-ureidopropyl trimethoxy silane.

2. The flexible coating of claim 1, further comprising an additive.

3. The flexible coating of claim 2 wherein said additive is a pharmacological compound.

4. The flexible coating of claim 1 wherein said RTV silicone is methyltri-methoxy silane.

5. The flexible coating of claim 1 wherein said RTV silicone is methyltri-acetoxy silane.

6. The flexible coating of claim 1 wherein said urethane is selected from the group consisting of 4,4-methylenediphenol diisocyanante, 1,4-butanediol and polytetramethylene glycol.

7. The flexible coating of claim 1 further comprising a dye or pigment.

8. The flexible coating of claim 3 wherein said pharmacological compound is an anti-microbial selected from a group consisting of chorhexidene acetate, chlorhexidine gluconate, chlorhexidine hydrochloride, chlorhexidine sulfate, silver acetate, silver benzoate, silver carbonate, silver iodate, silver iodide, silver lactate, silver chloride, silver laurate, silver nitrate, silver oxide, silver palmitate, silver protein, silver sulfadiazine, polymyxin, tetracycline, tobramycin, gentamicin, rifampician, bacitracin, neomycin, chloramphenical, oxolinic acid, norfloxacin, nalidix acid, pefloxacin, enoxacin and ciprofloxacin, ampicillin, amoxicillin, piracil, cephalosporins arid vancomycin.

9. The flexible coating of claim 3 wherein said pharmacological compound is an anti-fungal selected from a group consisting of tolnaftate, miconazole, fluconazole, clotrimazole, econazole, ketoconazole, itraconazole, terbinafine, amphotericin, nystatin and natamycin.

10. The flexible coating of claim 3 wherein said pharmacological compound is an phytochemical selected from a group consisting of grapefruit seed extract, tea tree oil and myrtle oil.

11. The flexible coating of claim 1 wherein said coating is flexible while allowing adhesion to deformable segments of a medical device.

12. The flexible coating of claim 3 wherein said coating further includes an emulsifier, wherein said emulsifier stabilizes in suspension said pharmaceutical additive.

13. The flexible coating of claim 12 wherein said emulsifier is selected from the group consisting of ethylene glycol disterate and ethylene glycol monosterate.

14. A flexible coating including RTV silicone and urethane for a silicone based medical device, the flexible coating being disposed on a deformable surface of the silicone based medical device and retaining adhesion to the deformable surface, wherein said RTV silicone is selected from the group consisting of methyltri-methoxy silane, methyltri-acetoxy silane, tetrachlorosilane, vinyl trimethoryl silane, organosilane ester tris[3-trimethoxysilyl)propyl] isocyanurate, bis[trimethoxysilyl)propyl] amine and gamma-ureidopropyl trimethoxy silane.

15. The flexible coating of claim 14, further comprising an additive.

16. The flexible coating of claim 15 wherein said additive is a medicinal compound.

17. A flexible silicon based medical device coating comprising RTV silicone and urethane said coating being adherently disposed on a deformable surface of said device, wherein said RTV silicone is selected from the group consisting of methyltri-methoxy silane, methyltri-acetoxy silane, tetrachlorosilane, vinyl trimethoryl silane, organosilane ester tris[3-trimethoxysilyl)propyl], isocyanurate, bis[trimethoxysilyl)propyl] amine and gamma-ureidopropyl trimethoxy silane.

18. The flexible coating of claim, 17 wherein said RTV silicone is methyltri-methoxy silane.

19. The flexible coating of claim 17 wherein said RTV silicone is methyltriacetoxy silane.

20. The flexible coating of claim 17 wherein said urethane is selected from the group consisting of 4,4-methylenediphenol diisocyanante, 1,4-butanediol and polytetramethylene glycol.

21. The flexible coating of claim 17 further comprising a dye or pigment.

22. The flexible coating of claim 17 further comprising a medicinal compound, wherein said medicinal compound is an anti-microbial selected from a group consisting of chorhexidene acetate, chlorhexidine gluconate, chlorhexidine hydrochloride, chlorhexidine sulfate, silver acetate, silver benzoate, silver carbonate, silver iodate, silver iodide, silver lactate, silver chloride, silver laurate, silver nitrate, silver oxide, silver palmitate, silver protein, silver sulfadiazine, polymyxin, tetracycline, tobramycin, gentamicin, rifampician, bacitracin, neomycin, chloramphenical, oxolinic acid, norfloxacin, nalidix acid, pefloxacin, enoxacin and ciprofloxacin, ampicillin, amoxicillin, piracil, cephalosporins and vancomycin.

23. The flexible coating of claim 16 wherein said medicinal compound is an anti-fungal selected from a group consisting of tolnaftate, miconazole, fluconazole, clotrimazole, econazole, ketoconazole, itraconazole, terbinafine, amphotericin, nystatin and natamycin.

24. The flexible coating of claim 16 wherein said medicinal compound is an phytochemical selected from a group consisting of grapefruit seed extract, tea tree oil and myrtle oil.

25. The flexible coating of claim 17 wherein said coating further includes an emulsifier, wherein said emulsifier stabilizes in suspension said medicinal additive.

26. The flexible coating of claim 25 wherein said emulsifier is selected from the group consisting of ethylene glycol disterate and ethylene glycol monostearate.

27. The flexible coating of claim 25 wherein said coating contains between 30 to 70 percent by weight urethane, between 10 to 30 percent by weight RTV silicone, between 15 to 50 percent by weight medicinal agent and between 2 to 6 percent by weight emulsifier.

28. A method for producing a coating for a medical article comprising: blending RTV silicone, urethane, in a solvent until dissolved, wherein said RTV silicone is selected from the group consisting of methyltri-methoxy silane, methyltri-acetoxy silane, tetrachlorosilane, vinyl trimethoryl silane, organosilane ester tris[3-(trimethoxysilyl)propyl] isocyanurate, bis[trimethoxysilyl)propyl] amine and gamma-ureidopropyl trimethoxy silane.

29. The method of claim 28 further comprising the step of blending an additive until dissolved.

30. The method of claim 29 wherein said additive is a medicinal compound.

31. The method of claim 28 wherein said RTV silicone is methyltri-methoxy silane.

32. The method of claim 28 wherein said RTV silicone is methyltriacetoxy silane.

33. The method of claim 28 wherein said solvent is selected from the group consisting of ethyl lactate, methylbenzoate, propolyacrylate and n-Methypyrrolidinone.

34. The method of claim 28 further comprising the step of blending into said coating an emulsifier wherein said emulsifier stabilizes in suspension said pharmacological compound.

35. The method of claim 28 wherein said solvent is selected from the group consisting of toluene, hexane, xylene, tetrahydrofuran and cyclohexanone.

36. The method of claim 28 wherein said solvent is selected from the group consisting of C1–12 alkylesters of carboxylic acids.

37. The method of claim 28 wherein said urethane is selected from the group consisting of 4,4-methylenediphenol diisocyanante, 1,4-butanediol and polytetramethylene glycol.

38. The method of claim 28 further comprising a medicinal compound, wherein said medicinal compound is selected from a group consisting of chorhexidene acetate, chlorhexidine gluconate, chlorhexidine hydrochloride, chlorhexidine sulfate, silver acetate, silver benzoate, silver carbonate, silver iodate, silver iodide, silver lactate, silver chloride, silver laurate, silver nitrate, silver oxide, silver palmitate, silver protein, silver sulfadiazine, polymyxin, tetracycline, tobramycin, gentamicin, rifampician, bacitracin, neomycin, chloramphenical, quinolone, oxolinic acid, norfloxacin, nalidix acid, pefloxacin, enoxacin, ciprofloxacin, ampicillin, amoxicillin, piracil, cephalosporins and vancomycin.

39. The method of claim 30 wherein said medicinal compound is an anti-fungal selected from a group consisting of tolnaftate, miconazole, fluconazole, clotrimazole, econazole, ketoconazole, itraconazole, terbinafine, amphotericin, nystatin and natamycin.

40. The method of claim 30 wherein said medicinal compound is a phytochemical selected from a group consisting of grapefruit seed extract, tea tree oil and myrtle oil.

41. A method of controlling the release rate of a medicinal additive from a coating vehicle comprising:

providing a coating vehicle including urethane, RTV silicone and a medicinal additive, wherein said RTV silicone is selected from the group consisting of methyltri-methoxy silane, methyltri-acetoxy silane, tetrachlorosilane, vinyl trimethoryl silane, organosilane ester tris[3-(trimethoxysilyl)propyl] isocyanurate, bis [trimethoxysilyl)propyl] amine and gamma-ureidopropyl trimethoxy silane;

determining a therapeutic dosing range of the pharmacological additive;

determining pharmacokinetic properties of the pharmacological additive; and adjusting concentration of the urethane to the RTV silicone to achieve a desired release rate.

* * * * *